United States Patent [19]
Buchroeder et al.

[11] Patent Number: 5,515,209
[45] Date of Patent: May 7, 1996

[54] LIGHT-WEIGHT HIGH-MAGNIFICATION CLINICAL VIEWER

[75] Inventors: Richard A. Buchroeder, Tucson, Ariz.; Charles H. Caplan, Middleton, Wis.

[73] Assignee: Orascoptic Research, Inc., Madison, Wis.

[21] Appl. No.: 115,166

[22] Filed: Aug. 31, 1993

[51] Int. Cl.⁶ .......................... G02B 13/00; G02B 23/00
[52] U.S. Cl. ........................ 359/744; 359/362; 359/399
[58] Field of Search ........................ 359/362–363, 359/365–366, 399–400, 404, 407, 432, 434, 636, 733–736, 744, 797, 816, 683

[56] References Cited

U.S. PATENT DOCUMENTS

| | | | |
|---|---|---|---|
| 1,197,742 | 9/1916 | Kellner | 359/744 |
| 1,395,822 | 11/1921 | Hastings | 359/399 |
| 1,507,111 | 9/1924 | Erfle | 359/744 |
| 3,438,688 | 4/1969 | Wehr | 359/432 |
| 3,897,133 | 7/1975 | Warner | 359/365 |
| 3,936,152 | 2/1976 | Aurin et al. | 359/733 |
| 4,070,098 | 1/1978 | Buchroeder | 359/725 |
| 4,278,330 | 7/1981 | Buchroeder | 359/676 |
| 4,557,567 | 12/1985 | Azumi et al. | 359/683 |
| 4,761,064 | 8/1988 | Mercado et al. | 359/797 |
| 5,191,470 | 3/1993 | Wickholm et al. | 359/816 |
| 5,264,962 | 11/1993 | Kho | 359/362 |

*Primary Examiner*—Thong Q. Nguyen
*Attorney, Agent, or Firm*—Fitch, Even, Tabin & Flannery

[57] ABSTRACT

The light-weight high-magnification clinical viewer includes a three-element objective lens and a two-element eyepiece lens. Use of multiple lenses allows for a more compact package. The doublet eyepiece lens serves to reduce chromatic aberration at high magnification. The triplet objective serves to avoid vignetting while providing a wide field of view and reduced chromatic aberration. Image quality is further enhanced, while keeping the weight of the viewer down, through the use in the objective of light-weight high index glass.

3 Claims, 1 Drawing Sheet

LIGHT-WEIGHT HIGH-MAGNIFICATION CLINICAL VIEWER

CROSS REFERENCE TO RELATED APPLICATION

This invention is related to an application entitled "LIGHT-WEIGHT THREE-ELEMENT CLINICAL VIEWER", (Ser. No. 08/114,870, filed on even date herewith and assigned to the same assignee as the assignee of the present invention, now U.S. Pat. No. 5,463,500.

BACKGROUND OF THE INVENTION

A. Field of the Invention

The present invention relates to magnification viewers worn by surgeons and dentists. In particular, it relates to a compact, light-weight, comfortable-to-wear, high magnification viewer having an extremely wide field of view and good image quality.

B. Description of the Prior Art

Magnification viewers are worn by dentists and surgeons for extended periods of time during clinical procedures so as to provide clarity of view while avoiding a "hunched-over" position that can result in debilitating neck and back strain, which can have an adverse effect on the success of the operation. By permitting the clinician to operate at a greater working distance from the patient, higher magnification viewers also reduce the clinician's exposure to aerosols.

Because clinicians use magnification viewers during surgery and other procedures requiring manual precision, it is important that they be light-weight, comfortable, and have good clarity and wide field of vision while providing high magnification.

Clinical magnification viewers are generally made according to the "Galilean telescope" design, having a single objective lens and a single eyepiece lens. Galilean telescopes are characterized by relatively narrow fields of view which are mainly limited by the diameter of the objective lens. The basic Galilean design, however, produces substantial chromatic aberration ("coloring") and, hence, poor image quality.

The magnification, or power, of a Galilean telescope is proportional to the focal length of the objective and inversely proportional to the focal length of the eyepiece. Overall viewer length is proportional to the sum of the focal lengths of the objective and eyepiece.

Since the viewer should be kept as short as possible to reduce torque on the nose and wearer discomfort, an eyepiece with a shorter focal length is usually employed when an increase in magnification is desired. However, to retain a good field of view without vignetting, the diameter of the objective must be increased. If this is done while keeping the focal length of the objective the same, the "speed" of the lens increases, which results in a lower resolution quality. It also mandates an excessively large package. One method of overcoming the "speed" problem is to use a more complicated objective lens, though at the cost of greatly increased weight and strain and discomfort to the wearer.

The so-called Kellner design (from Kellner, U.S. Pat. No. 1,197,742 "Lens System") in general use today contains a heavy doublet objective and a singlet eyepiece lens. While image quality is adequate at lower magnifications, at higher magnifications, excessive coloring results in poor image quality. Moreover, the field of view is relatively limited.

It is known that image quality in prior art magnification viewers can be enhanced by the use of "very high index flint glass". However, this method has not been in general use, since "very high index flint glass" makes the viewer too heavy for practical use.

SUMMARY OF THE INVENTION

Accordingly, it is an object of the present invention to provide a compact, light-weight, high-resolution, high-magnification viewer with a wide field of view that is comfortable to wear over extended periods of time.

A further object of the present invention is to provide a magnification viewer having better color quality than prior art magnification viewers.

A further object of the invention is to provide a magnification viewer having a wider field of view even at high magnification levels than the prior art magnification viewers.

A further object of the present invention is to provide a higher resolution magnification viewer while maintaining small diameter lenses than prior art magnification viewers.

A further object of the present invention is to provide a more compact magnification viewer than prior art viewers.

A further object is to provide a lighter-weight magnification viewer having superior image quality than previous magnification viewers.

A further object of the present invention is to provide a magnification viewer having thinner lens elements while improving image quality using lightweight high index glass.

In accordance with one embodiment of the invention, the magnification viewer includes a three-element objective lens and a two-element eyepiece lens. Use of multiple lenses allows for a more compact package. The doublet eyepiece lens serves to reduce chromatic aberration at high magnification. The triplet objective serves to avoid vignetting while providing a wide field of view and reduced chromatic aberration. Image quality is further enhanced, while keeping the weight of the viewer down, through the use in the objective of light-weight high index glass.

DETAILED DESCRIPTION OF THE INVENTION

Figure 1:
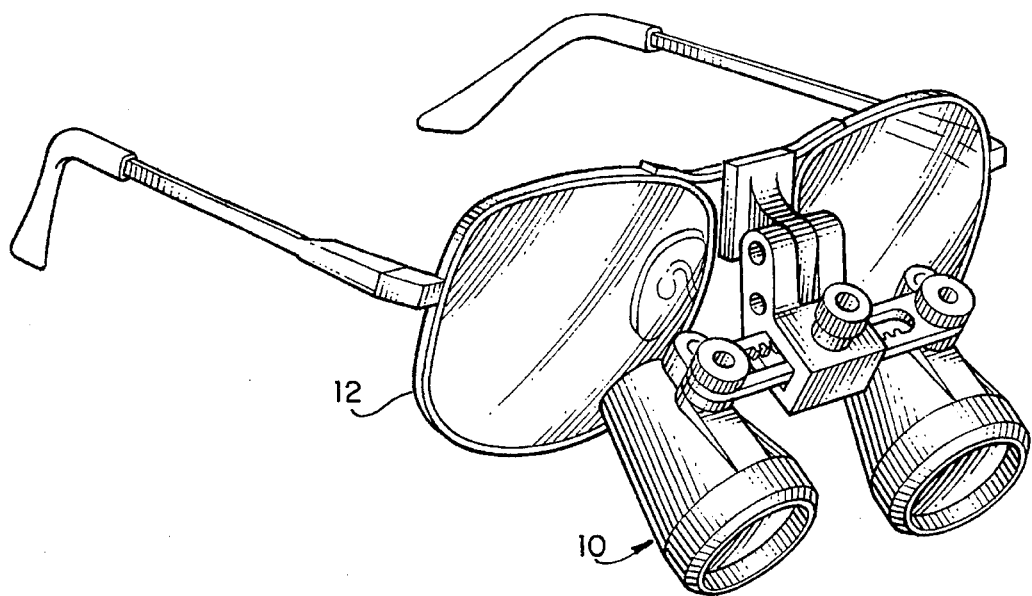
FIG. 1 is a perspective drawing of the viewer as attached to a pair of glasses.

One embodiment of the present invention, FIG. 1, includes a pair of magnification viewers 10, attached to a pair of eyeglasses, 12.

Figure 2:
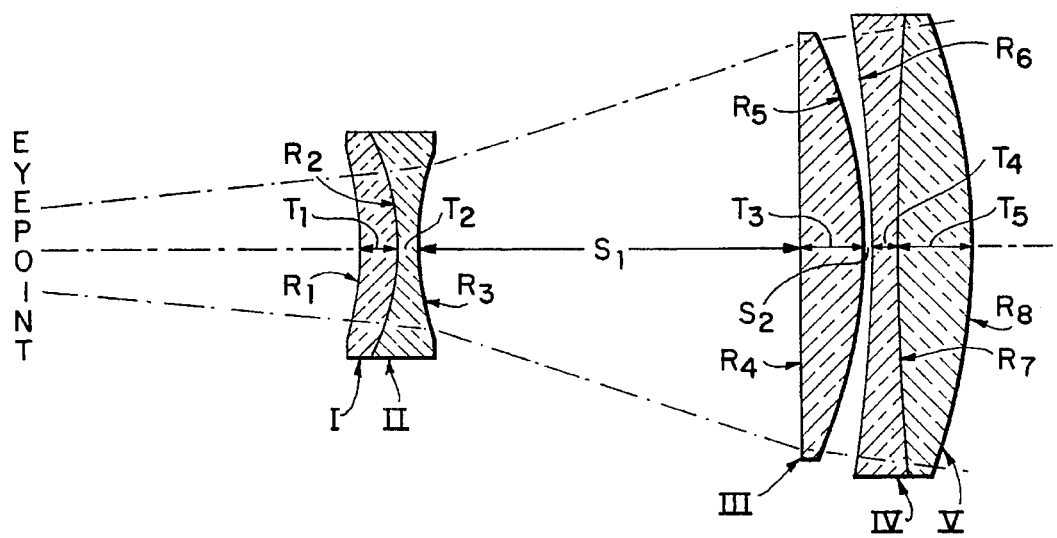
FIG. 2 is a diagram illustrating the viewer having a three-element objective and a two-element eyepiece.

Optics for the magnification viewer 10 are shown in FIG. 2. The viewer according to the invention includes a two-element eyepiece lens including elements I-II and a three-element objective lens including elements III-V. R1, R2, etc. represent the radii of respective refractive surfaces; $S_1$ and $S_2$ represent the thicknesses of the air spaces; and $T_1$, $T_2$ etc. represent the thicknesses of the lens elements.

The magnification viewer could be made of a single eyepiece and a single objective lens. However, chromatic aberrations would result in poor image quality. In the alternative, the objective lens could be made a doublet, as in the Kellner system. However, this reduces chromatic aberration only at low levels of magnification. Consequently, the eyepiece lens is made a doublet to reduce chromatic aberration at high levels of magnification.

Since magnification, or power, is proportional to the focal length of the objective and inversely proportional to the focal length of the eyepiece, high levels of magnification could be achieved by either decreasing the focal length of the eyepiece or increasing the focal length of the objective. However, the length of the viewer is proportional to the sum of the focal length of the eyepiece and the objective. Because a longer viewer, which results in higher torque on the bridge of the nose and greater wearer discomfort, is undesirable, magnification in the invention is achieved by decreasing the focal length of the eyepiece.

The shorter eyepiece, however, results in a decreased field of view or vignetting with a large field of view. This problem can be overcome through an increase in the diameter of the objective. However, the speed of a lens is equal to the ratio of the focal length and diameter. Thus, in order to maintain the short focal length of the objective while increasing its diameter, the lens becomes faster. This leads to aberrations which lower resolution quality.

Consequently, the invention employs a triplet objective, which results in reduced aberrations and enhanced image quality. The use of the triplet objective also makes for a more compact viewer.

Image quality can be improved still further through the use of very high index flint glass in the negative element of the objective. However, the use of very high index flint glass, coupled with a greater number of lens elements, of course, increases the weight of the viewer which, again, is undesirable.

Consequently, the invention uses "light-weight high index glass" of the type available from various manufacturers such as Schott and Ohara. The resulting triplet is reduced in weight while providing reduced aberrations and higher image quality.

Exemplary construction data for a viewer built according to the preferred embodiment shown in FIG. 2 are given in TABLE 1, TABLE 2, and TABLE 3. These represent, respectively, the "Viewer with Exemplary Standard Working Distance", "Viewer with Exemplary Long Working Distance", and "Viewer with Exemplary Extra Long Working Distance" configurations.

TABLE 1

| Viewer with Exemplary Standard Working Distance | | | | | |
|---|---|---|---|---|---|
| Element | $n_d$ | $v_d$ | Radius | Thickness | Separation |
| I | 1.805 | 25.4 | $R_1 = -24.420$ | $T_1 = 2.2$ | $S_1 = 23.80$ |
|   |       |      | $R_2 = -14.532$ |             | $S_2 = 0.50$ |
| II | 1.517 | 64.2 | $R_2 = -14.532$ | $T_2 = 1.2$ | |
|   |       |      | $R_3 = 17.620$ | | |
| III | 1.517 | 64.2 | $R_4 = $ FLAT | $T_3 = 4.0$ | |
|   |       |      | $R_5 = -30.786$ | | |
| IV | 1.805 | 25.4 | $R_6 = -70.775$ | $T_4 = 1.5$ | |
|   |       |      | $R_7 = 156.062$ | | |
| V | 1.607 | 56.7 | $R_7 = 156.062$ | $T_5 = 4.8$ | |
|   |       |      | $R_8 = -34.683$ | | |

TABLE 2

| Viewer with Exemplary Long Working Distance | | | | | |
|---|---|---|---|---|---|
| Element | $n_d$ | $v_d$ | Radius | Thickness | Separation |
| I | 1.805 | 25.4 | $R_1 = 21.900$ | $T_1 = 2.2$ | $S_1 = 23.81$ |
|   |       |      | $R_2 = -13.500$ |             | $S_2 = 0.50$ |
| II | 1.517 | 64.2 | $R_2 = -13.500$ | $T_2 = 1.2$ | |
|   |       |      | $R_3 = 17.500$ | | |
| III | 1.517 | 64.2 | $R_4 = $ FLAT | $T_3 = 4.0$ | |
|   |       |      | $R_5 = -30.786$ | | |
| IV | 1.805 | 25.4 | $R_6 = -70.775$ | $T_4 = 1.5$ | |
|   |       |      | $R_7 = 156.062$ | | |
| V | 1.607 | 56.7 | $R_7 = 156.062$ | $T_5 = 4.8$ | |
|   |       |      | $R_8 = -34.683$ | | |

TABLE 3

| Viewer with Exemplary Extra Long Distances | | | | | |
|---|---|---|---|---|---|
| Element | $n_d$ | $v_d$ | Radius | Thickness | Separation |
| I | 1.805 | 25.4 | $R_1 = -20.230$ | $T_1 = 2.2$ | $S_1 = 23.82$ |
|   |       |      | $R_2 = -12.700$ |             | $S_2 = 0.50$ |
| II | 1.517 | 64.2 | $R_2 = -12.700$ | $T_2 = 1.2$ | |
|   |       |      | $R_3 = 17.300$ | | |
| III | 1.517 | 64.2 | $R_4 = $ FLAT | $T_3 = 4.0$ | |
|   |       |      | $R_5 = -30.786$ | | |
| IV | 1.805 | 25.4 | $R_6 = -70.775$ | $T_4 = 1.5$ | |
|   |       |      | $R_7 = 156.062$ | | |
| V | 1.607 | 56.7 | $R_7 = 156.062$ | $T_5 = 4.8$ | |
|   |       |      | $R_8 = -34.683$ | | |

The radius, thickness, and separation dimensions are given in millimeters. Roman numerals identify the lens elements in their respective order from the eyepoint side to the object side; $n_d$ represents the refractive index of each element; $v_d$ is the Abbe dispersion number; $R_1$, $R_2$, etc., represent the radii of the respective refractive surfaces, in order, from the eyepoint side to the object side; $T_1$ and $S_1$ etc., represent the thicknesses of the lens elements and air spaces, respectively, from the eyepoint side to the object side, $T_1$ being the thickness of the first element I and $S_1$ being the thickness of the airspace between II and III. The thicknesses $T_1$ and $S_1$ etc. are measured along the optical centerline.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. A magnification viewer having a two-element eyepiece lens and a three-element objective lens; the magnification viewer having the design parameters represented in the following table:

| Viewer with Exemplary Standard Working Distance | | | | | |
|---|---|---|---|---|---|
| Element | $n_d$ | $v_d$ | Radius | Thickness | Separation |
| I | 1.805 | 25.4 | $R_1 = -24.420$ | $T_1 = 2.2$ | $S_1 = 23.80$ |
|   |       |      | $R_2 = -14.532$ |             | $S_2 = 0.50$ |
| II | 1.517 | 64.2 | $R_2 = -14.532$ | $T_2 = 1.2$ | |
|   |       |      | $R_3 = 17.620$ | | |
| III | 1.517 | 64.2 | $R_4 = $ FLAT | $T_3 = 4.0$ | |
|   |       |      | $R_5 = -30.786$ | | |
| IV | 1.805 | 25.4 | $R_6 = -70.775$ | $T_4 = 1.5$ | |
|   |       |      | $R_7 = 156.062$ | | |

Viewer with Exemplary Standard Working Distance

| Element | $n_d$ | $v_d$ | Radius | Thickness | Separation |
|---|---|---|---|---|---|
| V | 1.607 | 56.7 | $R_7 = 156.062$<br>$R_8 = -34.683$ | $T_5 = 4.8$ | | wherein the Roman numerals I and II identify the two lens elements of the eyepiece lens, and the Roman numerals III-V identify the three lens elements of the objective lens, from the eyepoint side to the object side; $n_d$ represents the refractive index of each element; $v_d$ is the Abbe dispersion number; $R_1$–$R_8$ represent the radii, in millimeters, of the respective refractive surfaces, in order, from the eyepoint side to the object side; $T_1$–$T_5$ and $S_1$–$S_2$ represent the thicknesses, in millimeters, of the lens elements and air spaces, respectively, from the eyepoint side to the object side measured along an optical centerline.

2. A magnification viewer having a two-element eyepiece lens and a three-element objective lens; the magnification viewer having the design parameters represented in the following table:

| Element | $n_d$ | $v_d$ | Radius | Thickness | Separation |
|---|---|---|---|---|---|
| I | 1.805 | 25.4 | $R_1 = -21.900$<br>$R_2 = 13.500$ | $T_1 = 2.2$ | $S_1 = 23.81$<br>$S_2 = 0.50$ |
| II | 1.517 | 64.2 | $R_2 = -13.500$<br>$R_3 = 17.500$ | $T_2 = 1.2$ | |
| III | 1.517 | 64.2 | $R_4 = $ FLAT<br>$R_5 = -30.786$ | $T_3 = 4.0$ | |
| IV | 1.805 | 25.4 | $R_6 = -70.775$<br>$R_7 = 156.062$ | $T_4 = 1.5$ | |
| V | 1.607 | 56.7 | $R_7 = 156.062$<br>$R_8 = -34.683$ | $T_5 = 4.8$ | | wherein the Roman numerals I and II identify the two lens elements of the eyepiece lens, and the Roman numerals III-V identify the three lens elements of the objective lens, from the eyepoint side to the object side; $n_d$ represents the refractive index of each element; $v_d$ is the Abbe dispersion number; $R_1$–$R_8$ represent the radii, in millimeters, of the respective refractive surfaces, in order, from the eyepoint side to the object side; $T_1$–$T_5$ and $S_1$–$S_2$ represent the thicknesses, in millimeters, of the lens elements and air spaces, respectively, from the eyepoint side to the object side measured along an optical centerline.

3. A magnification viewer having a two-element eyepiece lens and a three-element objective lens; the magnification viewer having the design parameters represented in the following table:

| Element | $n_d$ | $v_d$ | Radius | Thickness | Separation |
|---|---|---|---|---|---|
| I | 1.805 | 25.4 | $R_1 = -20.230$<br>$R_2 = -12.700$ | $T_1 = 2.2$ | $S_1 = 23.82$<br>$S_2 = 0.50$ |
| II | 1.517 | 64.2 | $R_2 = -12.700$<br>$R_3 = 17.300$ | $T_2 = 1.2$ | |
| III | 1.517 | 64.2 | $R_4 = $ FLAT<br>$R_5 = -30.786$ | $T_3 = 4.0$ | |
| IV | 1.805 | 25.4 | $R_6 = -70.775$<br>156.062 | $T_4 = 1.5$ | |
| V | 1.607 | 56.7 | $R_7 = 156.062$<br>$R_8 = -34.683$ | $T_5 = 4.8$ | | wherein the Roman numerals I and II identify the two lens elements of the eyepiece lens, and the Roman numerals III-V identify the three lens elements of the objective lens, from the eyepoint side to the object side; $n_d$ represents the refractive index of each element; $v_d$ is the Abbe dispersion number; $R_1$–$R_8$ represent the radii, in millimeters, of the respective refractive surfaces, in order, from the eyepoint side to the object side; $T_1$–$T_5$ and $S_1$14 $S_2$ represent the thicknesses, in millimeters, of the lens elements and air spaces, respectively, from the eyepoint side to the object side measured along an optical centerline.

\* \* \* \* \*

UNITED STATES PATENT AND TRADEMARK OFFICE
CERTIFICATE OF CORRECTION

PATENT NO. : 5,515,209
DATED : May 7, 1996
INVENTOR(S) : Caplan et al

It is certified that error appears in the above-indentified patent and that said Letters Patent is hereby corrected as shown below:

| Column | Line | |
|---|---|---|
| 5 | 19 | Delete "an" and insert --the-- therefor; |
| 5 | 21 | Delete "obiective" to --objective-- therefor; |
| 5 | | In the table of claim 2: Under "Radius" delete "$R_2 = 13.500$" and insert --$R_2 = -13.500$-- therefor; |
| 6 | 8 | Delete "an" and insert --the-- therefor; |
| 6 | | In the table of claim 3: Under "Radius" delete "156.062" and insert --$R_7 = -156.062$-- therefor; |
| 6 | 33 | Delete "$S_1$ 14 $S_2$" and insert --$S_1$, - $S_2$-- therefor; and |
| 6 | 36 | Delete "an" and insert --the-- therefor. |

Signed and Sealed this

Third Day of September, 1996

Attest:

BRUCE LEHMAN

Attesting Officer    Commissioner of Patents and Trademarks